United States Patent [19]

Krämer et al.

[11] 4,254,132
[45] * Mar. 3, 1981

[54] COMBATING FUNGI WITH 2-ACYLOXY-1-AZOLYL-3,3-DIMETHYL-2-PHENOXY-BUTANES

[75] Inventors: Wolfgang Krämer; Karl H. Büchel, both of Wuppertal; Paul-Ernst Frohberger, Leverkusen; Wilhelm Brandes, Leichlingen, all of Fed. Rep. of Germany

[73] Assignee: Bayer Aktiengesellschaft, Leverkusen, Fed. Rep. of Germany

[*] Notice: The portion of the term of this patent subsequent to Jan. 16, 1996, has been disclaimed.

[21] Appl. No.: 14,771

[22] Filed: Feb. 22, 1979

[30] Foreign Application Priority Data

Mar. 18, 1978 [DE] Fed. Rep. of Germany ....... 2811919

[51] Int. Cl.³ .................... A01N 43/50; A01N 43/64; C07D 233/60; C07D 249/08
[52] U.S. Cl. .................... 424/269; 424/245; 424/273 R; 548/101; 548/262; 548/341; 568/308; 568/316; 568/391; 568/392; 568/394; 568/414; 568/419
[58] Field of Search .......................... 260/299, 308 R; 548/341, 101, 262; 424/269, 273 R, 245

[56] References Cited

U.S. PATENT DOCUMENTS

| 4,134,988 | 1/1979 | Kramer et al. | 548/341 |
| 4,145,428 | 3/1979 | Kramer et al. | 260/299 |
| 4,154,842 | 5/1979 | Kramer et al. | 548/341 |

FOREIGN PATENT DOCUMENTS

| 2632601 | 1/1978 | Fed. Rep. of Germany | 260/308 R |
| 2632603 | 1/1978 | Fed. Rep. of Germany | 260/308 R |

Primary Examiner—Alton D. Rollins
Attorney, Agent, or Firm—Sprung, Felfe, Horn, Lynch & Kramer

[57] ABSTRACT

A 2-acyloxy-1-azolyl-3,3-dimethyl-2-phenoxy-butane of the formula

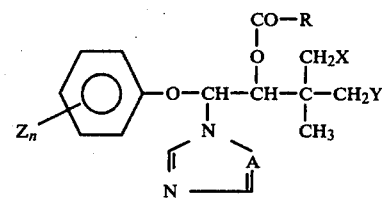

in which
A represents a nitrogen atom or the CH group,
R represents alkyl, alkenyl, alkynyl, alkoxy, alkoxyalkyl, cycloalkyl, halogenoalkyl, optionally substituted phenyl, optionally substituted phenylalkyl, optionally substituted phenoxyalkyl, alkylamino, dialkylamino, optionally substituted phenylamino, halogenalkylamino, alkoxycarbonylamino, or alkoxyalkylamino,
X represents hydrogen, halogen or alkylcarbonyloxy,
Y represents halogen or alkylcarbonyloxy,
Z represents halogen, alkyl, cycloalkyl, alkoxy, halogenoalkyl, alkylthio, alkoxycarbonyl, optionally substituted phenyl, optionally substituted phenoxy, optionally substituted phenylalkyl, cyano or nitro, and
n represents 0, 1, 2, 3, 4 or 5, the substituents Z being selected independently of one another when n is 2 or more,
and salts and complexes thereof which possess fungicidal properties.

11 Claims, No Drawings

COMBATING FUNGI WITH 2-ACYLOXY-1-AZOLYL-3,3-DIMETHYL-2-PHENOXY-BUTANES

The present invention relates to and has for its objects the provision of particular new 2-acyloxy-1-azolyl-3,3-dimethyl-2-phenoxy-butanes which possess fungicidal properties, active compositions in the form of mixtures of such compounds with solid and liquid dispersible carrier vehicles, and methods for producing such compounds and for using such compounds in a new way especially for combating pests, e.g. fungi, with other and further objects becoming apparent from a study of the within specification and accompanying examples.

It has already been disclosed that acylated triazolyl- and imidazolyl-O,N-acetals, such as, in particular, 2-acyloxy-3,3-dimethyl-1-phenoxy-1-(1,2,4-triazol-1-yl)- and -(imidazol-1-yl)-butanes which are substituted in the phenyl part, have good fungicidal properties (see DE-OS (German Published Specification) No. 2,600,799 and DE-OS (German Published Specification) No. 2,604,761). However, their action is not always completely satisfactory, especially when low amounts and concentrations are used.

The present invention now provides, as new compounds, the acylated 1-azolyl-2-hydroxy-butane derivatives of the general formula

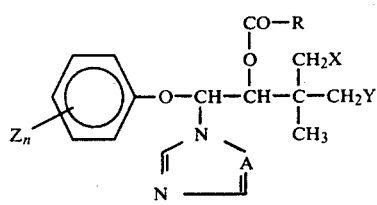

(I)

in which
A represents a nitrogen atom or the CH group,
R represents alkyl, alkenyl, alkynyl, alkoxy, alkoxyalkyl, cycloalkyl, halogenoalkyl, optionally substituted phenyl, optionally substituted phenylalkyl, optionally substituted phenoxyalkyl, alkylamino, dialkylamino, optionally substituted phenylamino, halogenoalkylamino, alkoxycarbonylamino or alkoxyalkylamino,
X represents hydrogen, halogen or alkylcarbonyloxy,
Y represents halogen or alkylcarbonyloxy,
Z represents halogen, alkyl, cycloalkyl, alkoxy, halogenoalkyl, alkylthio, alkoxycarbonyl, optionally substituted phenyl, optionally substituted phenoxy, optionally substituted phenylalkyl, cyano or nitro and
n represents 0, 1, 2, 3, 4 or 5, the substituents Z being selected independently of one another when n is 2 or more, and their physiologically acceptable acid addition salts and metal salt complexes. They have powerful fungicidal properties.

Preferably, R represents straight-chain or branched alkyl with 1 to 8 (especially 1 to 6) carbon atoms, straight-chain or branched alkenyl or alkynyl with in either case 2 to 4 carbon atoms, halogenoalkyl with 1 or 2 carbon atoms and 1 to 5 halogen atoms (especially fluorine and/or chlorine), alkoxy with 1 to 4 carbon atoms, alkoxyalkyl with 1 to 4 carbon atoms in each alkyl part, cycloalkyl with 5 to 7 carbon atoms (especially cyclohexyl), phenyl, phenylalkyl with 1 or 2 carbon atoms in the alkyl part, phenoxyalkyl with 1 or 2 carbon atoms in the alkyl part [the three last-mentioned radicals R optionally carrying one or more substituents on the phenyl nucleus selected from halogen, cyano, nitro and alkyl with 1 or 2 carbon atoms], alkylamino with 1 to 12 carbon atoms, dialkylamino with 1 to 4 (especially 1 or 2) carbon atoms in each alkyl part, halogenoalkylamino with up to 4 carbon atoms and up to 5 identical or different halogen atoms (especially fluorine and/or chlorine atoms), alkoxycarbonylamino with 1 to 4 carbon atoms in the alkyl part, alkoxyalkylamino with 1 to 4 carbon atoms in each alkyl part or phenylamino which optionally carries on or more substituents selected from halogen, nitro, cyano, straight-chain or branched alkyl with 1 to 4 carbon atoms, alkoxy and alkylthio with in either case 1 or 2 carbon atoms, halogenoalkyl with up to 2 carbon atoms and up to 5 identical or different halogen atoms (especially fluorine and/or chlorine atoms) and alkoxycarbonylalkenyl with 1 to 4 carbon atoms in the alkyl part and 2 to 4 carbon atoms in the alkenyl part;

X represents hydrogen, halogen (especially chlorine or bromine) or alkylcarbonyloxy with 1 to 4 carbon atoms in the alkyl part;

Y represents halogen (especially chlorine or bromine) or alkoxycarbonyloxy with 1 to 4 carbon atoms in the alkyl part;

Z represents halogen, cyano, nitro, straight-chain or branched alkyl with up to 4 carbon atoms, cycloalkyl with 5 to 7 carbon atoms (especially cyclohexyl), halogenoalkyl with up to 2 carbon atoms and up to 5 halogen atoms (especially fluorine and/or chlorine atoms), alkoxycarbonyl with a total of up to 5 carbon atoms, alkoxy or alkylthio with in either case up to 2 carbon atoms, phenyl or phenoxy [either of which may carry one or more substituents selected from halogen, amino, cyano, nitro and alkyl with 1 to 2 carbon atoms] or phenylalkyl with 1 or 2 carbon atoms in the alkyl part, which optionally may be substituted in the alkyl part by alklycarbonyloxy with a total of up to 3 carbon atoms and may be substituted in the phenyl part by halogen, nitro or cyano; and n represents 0, 1, 2 or 3.

The compounds of the formula (I) possess two asymmetric carbon atoms; they can therefore exist in the erythro form and in the threo form. In both cases, they exist predominantly as racemates.

Surprisingly, the acylated 1-azolyl-2-hydroxy-butane derivatives according to the invention exhibit a considerably higher fungicidal activity, in particular against species of rust and mildew, than the acylated triazolyl- and imidazolyl-O,N-acetals known from the state of the art, which are very closely related compounds chemically and from the point of view of their action. The substances according to the invention thus represent an enrichment of the art.

Those compounds of the formula (I) in which R represents methyl, ethyl, isobutyl, chloromethyl, dichloromethyl, methacryl, cyclohexyl, optionally monosubstituted or polysubstituted phenyl or phenoxymethyl with chlorine, bromine or methyl as substituents, and furthermore methoxy, ethoxy, isopropoxy, butoxy or isobutoxy, methyl- and ethylamino, dimethylamino, phenylamino, chlorophenylamino, chloroethylamino, methoxycarbonylamino, ethoxycarbonylamino or methoxymethylamino, X represents hydrogen, chlorine, bromine or methylcarbonyloxy, Y represents chlorine, bromine or methylcarbonyloxy, Z represents chlorine, bromine, methyl, ethyl, cyclohexyl, methoxy, methylthio, trifluoromethyl, methoxycarbonyl, cyano, nitro or phenyl, benzyl or phenoxy which are optionally substituted by chlorine, and n represents 0, 1 or 2 are very particularly preferred.

Specific compounds of the general formula (I) which may be mentioned, in addition to the compounds disclosed in the preparative examples, are the following: 1-(4-bromophenoxy)-1-(1,2,4-triazol-1-yl)-2-isobutylcarbonyloxy-3,3-dimethyl-4-chloro-butane, 1-(2,4-dichlorophenoxy)-1-(1,2,4-triazol-1-yl)-2-methylcarbamoyloxy-3,3-dimethyl-4-chlorobutane, 1-(2,4-dichlorophenoxy)-1-(1,2,4-triazol-1-yl)-2-ethylcarbonyloxy-3,3-dimethyl-4-chloro-butane, 1-(4-methoxyphenoxy)-1-(1,2,4-triazol-1-yl)-2-acetoxy-3,3-dimethyl-4-chloro-butane,1-(3-trifluoromethylphenoxy)-1-(1,2,4-triazol-1-yl)-2-chloroacetoxy-3,3-dimethyl-4-chloro-butane, 1-(4-methoxycarbonylphenoxy)-1-(1,2,4-triazol-1-yl)-2-dichloroacetoxy-3,3-dimethyl-4-bromo-butane, 1-(4-biphenylyloxy)-1-(1,2,4-triazol-1-yl)-2-methylcarbamoyloxy-3,3-dimethyl-4-chloro-butane, 1-(4-bromophenoxy)-1-(1,2,4-triazol-1-yl)-2-isobutylcarbonyloxy-3,3-dimethyl-4-bromo-butane, 1-(2,4-dichlorophenoxy)-1-(1,2,4-triazol-1-yl)-2-methylcarbamoyloxy-3,3-dimethyl-4-bromo-butane, 1-(2,4-dichlorophenoxy)-1-(1,2,4-triazol-1-yl)-2-ethylcarbonyloxy-3,3-dimethyl-4-bromo-butane, 1-(4-methoxyphenoxy)-1-(1,2,4-triazol-1-yl)-2-acetoxy-3,3-dimethyl-4-bromo-butane, 1-(3-trifluoromethylphenoxy)-1-(1,2,4-triazol-1-yl)-2-chloroacetoxy-3,3-dimethyl-4-bromo-butane, 1-(4-methoxycarbonylphenoxy)-1-(1,2,4-triazol-1-yl)-2-dichloroacetoxy-3,3-dimethyl-4-chloro-butane, 1-(4-biphenylyloxy)-1-(1,2,4-triazol-1-yl)-2-methylcarbamoyloxy-3,3-dimethyl-4-bromo-butane, 1-(4-biphenylyloxy)-1-(1,2,4-triazol-1-yl)-2-methylcarbamoyloxy-3,3-dimethyl-4-acetoxy-butane, 1-(4-biphenyloxy)-1-(1,2,4-triazol-1-yl)-2-ethylcarbamoyloxy-3,3-dimethyl-4-chloro-butane, 1-(4-biphenylyloxy)-1-(1,2,4-triazol-1-yl)-2-ethylcarbamoyloxy-3,3-dimethyl-4-bromo-butane, 1-(4-biphenylyloxy)-1-(1,2,4-triazol-1-yl)-2-ethylcarbamoyloxy-3,3-dimethyl-4-acetoxy-butane, 1-(4-biphenylyloxy)-1-(1,2,4-triazol-1-yl)-2-methoxymethylcarbamoyloxy-3,3-dimethyl-4-chloro-butane, 1-(4-biphenylyloxy)-1-(1,2,4-triazol-1-yl)-2-methoxymethylcarbamoyloxy-3,3-dimethyl-4-bromo-butane, 1-(4-biphenylyloxy)-1-(1,2,4-triazol-1-yl)-2-methoxymethylcarbamoyloxy-3,3-dimethyl-4-acetoxy-butane, 1-(4-biphenylyloxy)-1-(1,2,4-triazol-1-yl)-2-ethoxymethylcarbamoyloxy-3,3-dimethyl-4-chloro-butane, 1-(4-biphenylyloxy)-1-(1,2,4-triazol-1-yl)-2-ethoxymethylcarbamoyloxy-3,3-dimethyl-4-bromo-butane, 1-(4-biphenylyloxy)-1-(1,2,4-triazol-1-yl)-2-ethoxymethylcarbamoyloxy-3,3-dimethyl-4-acetoxy-butane, 1-(4-biphenylyloxy)-1-(1,2,4-triazol-1-yl)-2-methoxycarbonylcarbamoyloxy-3,3-dimethyl-4-chloro-butane, 1-(4-biphenylyloxy)-1-(1,2,4-triazol-1-yl)-2-methoxycarbonylcarbamoyloxy-3,3-dimethyl-4-bromo-butane, 1-(4-biphenylyloxy)-1-(1,2,4-triazol-1-yl)-2-ethoxycarbonylcarbamoyloxy-3,3-dimethyl-4-chloro-butane, 1-(4-biphenylyloxy)-1-(1,2,4-triazol-1-yl)-2-ethoxycarbonylcarbamoyloxy-3,3-dimethyl-4-chloro-butane, 1-(4-biphenylyloxy)-1-(1,2,4-triazol-1-yl)-2-ethoxycarbonylcarbamoyloxy-3,3-dimethyl-4-bromo-butane, 1-(4-biphenylyloxy)-1-(1,2,4-triazol-1-yl)-2-phenylcarbamoyloxy-3,3-dimethyl-4-chloro-butane, 1-(4-biphenylyloxy)-1-(1,2,4-triazol-1-yl)-2-phenylcarbamoyloxy-3,3-dimethyl-4-bromo-butane, 1-(4-biphenylyloxy)-1-(1,2,4-triazol-1-yl)-2-(4-chlorophenylcarbamoyloxy)-3,3-dimethyl-4-chloro-butane, 1-(4-biphenylyloxy)-1-(1,2,4-triazol-1-yl)-2-(4-chlorophenylcarbamoyloxy)-3,3-dimethyl-4-bromo-butane, 1-(4-biphenylyloxy)-1-(1,2,4-triazol-1-yl)-2-dimethylcarbamoyloxy-3,3-dimethyl-4-chloro-butane, 1-(4-biphenylyloxy)-1-(1,2,4-triazol-1-yl)-2-dimethylcarbamoyloxy-3,3-dimethyl-4-bromo-butane, 1-(4-biphenylyloxy)-1-(1,2,4-triazol-1-yl)-2-dimethylcarbamoyloxy-3,3-dimethyl-4-acetoxy-butane, 1-(4-biphenyloxy)-1-(1,2,4-triazol-1-yl)-2-methoxycarbonyloxy-3,3-dimethyl-4-chloro-butane, 1-(4-biphenylyloxy)-1-(1,2,4-triazol-1-yl)-2-methoxycarbonyloxy-3,3-dimethyl-4-bromo-butane, 1-(4'-chloro-4-biphenylyloxy)-1-(1,2,4-triazol-1-yl)-2-acetoxy-3,3-dimethyl-4-chloro-butane, 1-(4'-chloro-4-biphenylyloxy)-1-(1,2,4-triazol-1-yl)-2-acetoxy-3,3-dimethyl-4-bromo-butane, 1-(4'-chloro-4-biphenylyloxy)-1-(1,2,4-triazol-1-yl)-2,4-diacetoxy-3,3-dimethyl-butane, 1-(4-phenoxyphenoxy)-1-(1,2,4-triazol-1-yl)-2-acetoxy-3,3-dimethyl-4-chloro-butane, 1-(4'-chloro-4-phenoxyphenoxy)-1-(1,2,4-triazol-1-yl)-2-acetoxy-3,3-dimethyl-4-chloro-butane, 1-(4-cyanophenoxy)-1-(1,2,4-triazol-1-yl)-2-acetoxy-3,3-dimethyl-4-chloro-butane, 1-(4-nitrophenoxy)-1-(1,2,4-triazol-1-yl)-2-acetoxy-3,3-dimethyl-4-chloro-butane, 1-(4'-chloro-4-biphenylyloxy)1-(1,2,4-triazol-1-yl)-2-acetoxy-3,3-di(chloromethyl)-butane, 1-(4-biphenylyloxy)-1-(1,2,4-triazol-1-yl)-2-methylcarbamoyloxy-3,3-di(chloromethyl)-butane, 1-(4-biphenylyloxy)-1-(1,2,4-triazol-1-yl)-2-methylcarbamoyloxy-3,3-dimethyl-4-bromo-butane, 1-(4-chlorophenoxy)-1-(1,2,4-triazol-1-yl)-2-methacrylocarbonyloxy-3,3-dimethyl-4-bromo-butane, 1-(4-chlorophenoxy)-1-(1,2,4-triazol-1-yl)-2,4-diacetoxy-3,3-dimethyl-butane, 1-(4-chlorophenoxy)-1-(1,2,4-triazol-1-yl)-2,4-diacetoxy-3-acetoxymethyl-3-methyl-butane, 1-(4-bromophenoxy)-1-(imidazol-1-yl)-2-isobutylcarbonyloxy-3,3-dimethyl-4-chloro-butane, 1-(2,4-dichlorophenoxy)-1-(imidazol-1-yl)-2-methylcarbamoyloxy-3,3-dimethyl-4-chloro-butane, 1-(2,4-dichlorophenoxy)-1-(imidazol-1-yl)-2-ethylcarbonyloxy-3,3-dimethyl-4-chloro-butane, 1-(4-methoxyphenoxy)-1-(imidazol-1-yl)-2-acetoxy-3,3-dimethyl-4-chloro-butane, 1-(3-trifluoromethylphenoxy)-1-(imidazol-1-yl)-2-chloroacetoxy-3,3-dimethyl-4-chloro-butane, 1-(4-methoxycarbonylphenoxy)-1-(imidazol-1-yl)-2-dichloroacetoxy-3,3-dimethyl-4-bromo-butane, 1-(4-biphenylyloxy)-1-(imidazol-1-yl)-2-methylcarbamoyloxy-3,3-dimethyl-4-chloro-butane, 1-(4-biphenylyloxy)-1-(imidazol-1-yl)-2-methylcarbamoyloxy-3,3-dimethyl-4-bromo-butane, 1-(4-biphenylyloxy)-1-(imidazol-1-yl)-2-methylcarbamoyloxy-3,3-dimethyl-4-acetoxy-butane, 1-(4-biphenylyloxy)-1-(imidazol-1-yl)-2-ethylcarbamoyloxy-3,3-dimethyl-4-chloro-butane, 1-(4-biphenylyloxy)-1-(imidazol-1-yl)-2-ethylcarbamoyloxy-3,3-dimethyl-4-bromo-butane, 1-(4-biphenylyloxy)-1-(imidazol-1-yl)-2-ethylcarbamoyloxy-3,3-dimethyl-4-acetoxy-butane, 1-(4-biphenylyloxy)-1-(imidazol-1-yl)-2-methoxymethylcarbamoyloxy-3,3-dimethyl-4-chloro-butane, 1-(4-biphenylyloxy)-1-(imidazol-1-yl)-2-methoxymethylcarbamoyloxy-3,3-dimethyl-4-bromo-butane, 1-(4-biphenylyloxy)-1-(imidazole-1-yl)-2-methyoxymethylcarbamoyloxy-3,3-dimethyl-4-acetoxy-butane, 1-(4-biphenylyloxy)-1-(imidazol-1-yl)-2-ethoxymethylcarbamoyloxy-3,3-dimethyl-4-chloro-butane, 1-(4-biphenylyloxy)-1-(imidazol-1-yl)-2-ethoxymethylcarbamoyl-3,3-dimethyl-4-bromo-butane, 1-(4-biphenylyloxy)-1-(imidazol-1-yl)-2-ethoxymethylcarbamoyloxy-3,3-dimethyl-4-acetoxy-butane, 1-(4-biphenylyloxy)-1-(imidazol-1-yl)-2-methoxycarbonylcarbamoyloxy-3,3-dimethyl-4-chloro-butane, 1-(4-biphenylyloxy)-1-(imidazol-1-yl)-2-methoxycarbonylcarbamoyloxy-3,3-dimethyl-4-bromo-butane, 1-(4-biphenylyloxy)-1-(imidazol-1-yl)-2-ethoxycarbonylcarbamoyloxy-3,3-dimethyl-4-chloro-butane, 1-(4-biphenylyloxy)-1-(imidazol-1-yl)-2-ethoxycarbonylcarbamoyloxy-3,3-dimethyl-4-bromo-butane, 1-(4-biphenylyloxy)-1-(imidazol-1-yl)-2-phenylcarbamoyloxy-3,3-dimethyl-4-chloro-butane, 1-(4-biphenylyloxy)-1-(imidazol-1-yl)-2-phenylcarbamoyloxy-3,3-dimethyl-4-bromo-butane, 1-(4-biphenylyloxy)-1-(imidazol-1-yl)-2-(4-chloro-phenylcarbamoyloxy)-3,3-dimethyl-4-chloro-butane, 1-(4-biphenylyloxy)-1-(imidazol-1-yl)-2-(4-chlorophenylcarbamoyloxy)-3,3-dimethyl-4-bromo-butane, 1-(4-biphenylyloxy)-1-(imidazol-1-yl)-2-dimethylcarbamoyloxy-3,3-dimethyl-4-chloro-butane, 1-(4-biphenylyloxy)-1-(imidazol-1-yl)-2-dimethylcarbamoyloxy-3,3-dimethyl-4-bromo-butane, 1-(4-biphenylyloxy)-1-(imidazol-1-yl)-2-dimethylcarbamoyloxy-3,3-dimethyl-4-acetoxy-butane, 1-(4-biphenylyloxy)-1-(imidazol-1-yl)-2-methoxycarbonyloxy-3,3-dimethyl-4-chloro-butane and 1-(4-biphenylyloxy)-1-(imidazol-1-yl)-2-methoxycarbonyloxy-3,3-dimethyl-4-bromo-butane.

The invention also provides a process for the preparation of an acylated 1-azolyl-2-hydroxy-butane derivative of the formula (I) in which a 1-azolyl-2-hydroxy-butane derivative of the general formula

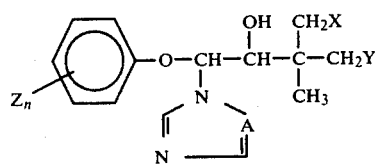

in which A, X, Y, Z and n have the meanings stated above, (a) is reacted with an acid halide of the general formula

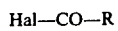

Hal—CO—R            (III), in which
R has the meaning stated above and
Hal represents halogen, preferably chlorine or bromine, is appropriate in the presence of a solvent and if appropriate in the presence of an acid-binding agent, or (b) is reacted with an acid anhydride of the general formula

R—CO—O—CO—R         (IV), in which R has the meaning stated above, in the presence of a solvent and if appropriate in the presence of a catalyst, or (c) is reacted with a ketene of the general formula

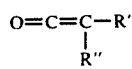

O=C=C—R'            (V),
     |
     R'' in which R' and R'' which may be identical or different, each represent hydrogen, alkyl, alkoxy, halogen, halogenoalkyl, alkenyl or optionally substituted phenyl, in the presence of a solvent and if appropriate in the presence of a catalyst, or (d) is reacted with an isocyanate of the general formula

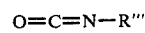

O=C=N—R'''          (VI), in which R''' represents alkyl, halogenoalkyl, alkoxycarbonyl, alkoxyalkyl or optionally substituted phenyl, in the presence of a solvent and if appropriate in the presence of a catalyst.

Furthermore, the acylated 1-azolyl-2-hydroxybutane derivatives of the formula (I) obtainable according to the invention can be converted into the salts by reaction with acids, or the corresponding metal salts complexes can be obtained by reaction with metal salts.

In some cases, it proves advantageous to prepare individual compounds in which X and/or Y represent alkylcarbonyloxy according to process (a) or (b), starting from such compounds of the formula (II) in which X and/or Y then represent the hydroxyl group (compare also the preparative examples hereinbelow).

If, for example, 1-(4-chlorophenoxy)-1-(1,2,4-triazol-1-yl)-3,3-dimethyl-4-chloro-butan-2-ol and dichloroacetyl chloride are used as starting substances in process variant (a), the course of the reaction can be represented by the equation which follows:

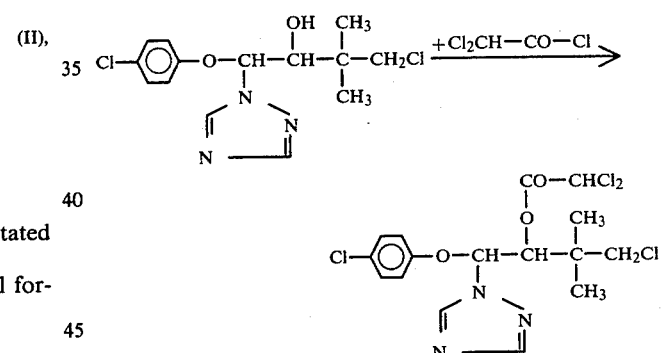

If, for example, 1-(4-chlorophenoxy)-1-(imidazol-1-yl)-3,3-dimethyl-4-chloro-butan-2-ol and acetic anhydride are used as starting substances in process variant (b), the course of the reaction can be represented by the equation which follows:

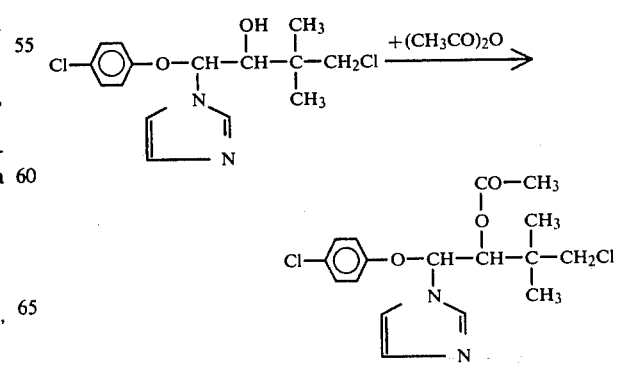

If, for example, 1-(2,4-dichlorophenoxy)-1-(1,2,4-triazol-1-yl)-3,3-dimethyl-4-bromo-butan-2-ol and 4-chlorophenyl isocyanate are used as starting substances in process variant (d), the course of the reaction can be represented by the equation which follows:

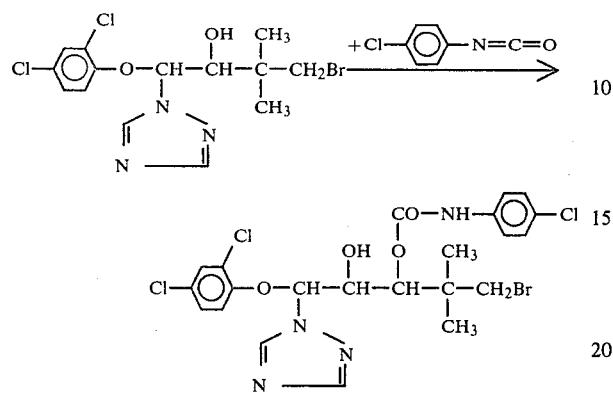

Reactions of 1-azolyl-2-hydroxy-butane derivatives of the formula (II) with a ketene of the formula (V) according to process variant (c) can be formulated in a corresponding manner.

1-Azolyl-2-hydroxy-butane derivatives of the formula (II) which can be used according to the invention are known (see DE-OS (German Published Specification) No. 2,632,603, DE-OS (German Published Specification) No. 2,632,602 and DE-OS (German Published Specification) No. 2,635,666), and they can be obtained by the processes described in the literature, by first reacting the corresponding 1-bromo-butan-2-ones with 1,2,4-triazole or imidazole in the presence of a diluent, for example acetone, and in the presence of an acid-binding agent, for example potassium carbonate, at temperatures between 60° and 120° C., reducing the 1-azolyl-butan-2-ones thereby obtained with complex hydrides, for example sodium borohydride, or with aluminum isopropylate, in a manner which is in itself known, if appropriate in the presence of a diluent, for example ethanol, at temperatures between 0° and 30° C., and isolating the products in the customary manner.

Acid halides of the formula (III) required in process variant (a) are known and they can be prepared by customary processes, for example by reacting carboxylic acids or alkali metal salts thereof with acid halides of phosphorus or sulphur. These methods are known from general textbooks of organic chemistry.

Acid anhydrides of the formula (IV) required in process variant (b) are known, and they can be prepared by known processes; thus, for example, by the action of acid chlorides on the alkali metal salts of the carboxylic acids. These processes are generally known.

The formula (V) provides a general definition of the ketenes required in process variant (c). In this formula, R' and R" are identical or different and preferably represent hydrogen, alkyl with 1 to 7, in particular 1 to 5, carbon atoms, alkenyl with up to 3 carbon atoms and halogenomethyl with 1 to 3 halogen atoms, in particular fluorine and chlorine. R' and R" also preferably represent halogen, such as, in particular, chlorine and bromine, alkoxy with 1 to 3 carbon atoms and phenyl which is optionally monosubstituted or polysubstituted, preferred substituents being: halogen, cyano, nitro or alkyl with 1 to 2 carbon atoms.

The ketenes of the formula (V) are known, or they can be prepared by known processes, for example by thermolysis of ketones or by dehydration of carboxylic acids (see Houben-Weyl, "Methoden der organischen Chemie" ("Methods of Organic Chemistry"), volume 7/4, Georg Thieme Verlag).

The formula (VI) provides a general definition of the isocyanates required in process variant (d). In this formula, R''' preferably represents straight-chain or branched alkyl with 1 to 12 carbon atoms, halogenalkyl with up to 4 carbon atoms and up to 5 identical or different halogen atoms, such as, in particular, fluorine and chlorine atoms, as well as alkoxycarbonyl and alkoxyalkyl with in each case 1 to 4 carbon atoms in each alkyl part. R''' also preferably represents phenyl which is optionally monosubstituted or polysubstituted, preferred possible substituents being: halogen, nitro, cyano, straight-chain or branched alkyl with 1 to 4 carbon atoms, alkoxy and alkylthio with in each case 1 or 2 carbon atoms, halogenoalkyl with up to 2 carbon atoms and up to 5 identical or different halogen atoms, such as, in particular, fluorine and chlorine atoms, as well as alkoxycarbonylalkenyl with 1 to 4 carbon atoms in the alkyl part and 2 to 4 carbon atoms in the alkenyl part.

Isocyanates of the formula (VI) are known, and they can be prepared by processes which are generally customary and known, for example by reacting amines with phosgene and subsequently heating the products.

Preferred possible solvents for the reaction according to process variant (a) are all the inert organic solvents, especially ketones, such as diethyl ketone, and in particular acetone and methyl ethyl ketone; nitriles, such as propionitrile, and in particular acetonitrile; ethers, such as tetrahydrofuran or dioxane; esters, such as ethyl acetate; aromatic hydrocarbons, such as benzene or toluene; and halogenated hydrocarbons, such as methylene chloride, carbon tetrachloride or chloroform. For simplicity, the acid chloride employed can also be used as the solvent, whereupon an appropriate excess becomes necessary.

The reaction temperature can be varied within a substantial range when carrying out process variant (a). In general, the reaction is carried out at from 0° to 100° C., preferably from 20° to 85° C. If a solvent is present, the reaction is appropriately carried out at the boiling point of the particular solvent. ;p If appropriate, process variant (a) can be carried out in the presence of an acid-binding agent (hydrogen halide acceptor). All the customary acid acceptors can be used as the acid-binding agents; these include organic bases, preferably tertiary amines, for example triethylamine, and furthermore inorganic bases, for example alkali metal hydroxides and alkali metal carbonates.

Equimolar amounts of the reactants are preferably employed in carrying out process variant (a). The compounds of the formula (I) are obtained in the form of their hydrohalides and can be isolated as such by precipitating them by adding an organic solvent, for example hexane, filtering them off and if appropriate purifying them by recrystallization. The compounds of the formula (I) can also be isolated in the form of the free bases by adding aqueous sodium bicarbonate solution to the reaction mixture and isolating the vbase by customary methods.

Preferred possible diluents for the reaction according to process variant (b) are all the inert organic solvents, especially the solvents listed for process variant (a), as well as the particular acid anhydrides of the formula (IV) used.

Catalysts which can preferably be used in process variants (b) and (c) are all the customary acid and basic catalysts, for example sulphuric acid, hydrochloric acid, hydrobromic acid, boron trifluoride, zinc chloride, sodium acetate, sodium benzoate, sodium carbonate, calcium oxide and magnesium oxide.

The reaction temperatures can be varied within a substantial range in carrying out process variant (b). In general, the reaction is carried out at from 0° to 150° C., preferably at from 80° to 120° C.

Equimolar amounts of the reactants are preferably employed in carrying out process variant (b). For simplicity, the acid anhydride of the formula (IV) employed can also be used as the solvent, whereupon an appropriate excess becomes necessary. Isolation of the compounds of the formula (I) is effected in the customary manner.

Preferred diluents for the reaction according to process variant (c) are all the inert organic solvents, especially the solvents listed for process variant (a).

The reaction temperatures can be varied within a certain range in carrying out process variant (c). In general, the reaction is carried out at from $-10°$ to $+70°$ C., preferably from 0° to 40° C.

Preferred diluents for the reaction according to process variant (d) are all the inert organic solvents, especially the solvents listed for process variant (a).

Catalysts which can preferably be used in process variant (d) are tertiary bases, such as triethylamine and pyridine, or organotin compounds, such as dibutyl-tin dilaurate.

The reaction temperatures can be varied within a substantial range in carrying out process variant (d). In general, the reaction is carried out at from 0° to 100° C., preferably from 20° to 40° C.

Equimolar amounts of the reactants are preferably employed in carrying out process variant (d). In order to isolate the compounds of the formula (I), the solvent is distilled off and the residue is worked up by customary methods.

All the physiologically acceptable acids can be used for the preparation of acid addition salts of the compounds of the formula (I). Preferred acids include hydrogen halide acids (for example hydrobromic acid and especially hydrochloric acid), phosphoric acid, nitric acid, sulphuric acid, monofunctional and bifunctional carboxylic acids and hydroxycarboxylic acids (for example acetic acid, maleic acid, succinic acid, fumaric acid, tartaric acid, citric acid, salicylic acid, sorbic acid and lactic acid) and sulphonic acids (for example p-toluenesulphonic acid and 1,5-naphthalenedisulphonic acid).

The salts of the compounds of the formula (I) can be obtained in a simple manner by customary salt formation methods, for example by dissolving a compound of the formula (I) in a suitable inert solvent and adding the acid, for example hydrochloric acid, and can be isolated in a known manner, for example by filtration, and if appropriate purified by washing with an inert organic solvent.

Salts of metals of main groups II to IV and of subgroups I and II and IV to VIII of the Periodic Table are preferably used for the preparation of metal salt complexes of the compounds of the formula (I), examples of metals which may be mentioned being copper, zinc, manganese, magnesium, tin, iron and nickel. Possible anions of the salts are those which are derived from physiological acids, especially hydrogen halide acids (for example hydrochloric acid and hydrobromic acid), phosphoric acid, nitric acid and sulphuric acid.

The metal salt complexes of the compounds of the formula (I) can be obtained in a simple manner by customary processes, for example by dissolving the metal salt in alcohol, for example ethanol, and adding the solution to the compound of the formula (I). The metal salt complexes can be isolated in a known manner, for example by filtration, and if appropriate purified by recrystallization.

The active compounds according to the invention exhibit a powerful fungitoxic action. They do not damage crop plants in the concentrations required for combating fungi. For these reasons, they are suitable for use as plant protection agents for combating fungi. Fungitoxic agents are employed in plant protection for combating Plasmodiophoromycetes, Comycetes, Chytridiomycetes, Zygomycetes, Ascomycetes, Basidiomycetes and Deuteromycetes.

The active compounds according to the invention have a broad spectrum of action and can be used against parasitic fungi which attack above-ground parts of plants or which attack the plants through the soil, as well as against seed-borne pathogens. They develop a particularly good activity against parasitic fungi on above-ground parts of plants.

As plant protection agents, the active compounds according to the invention can be used with particularly good success for combating those fungi which cause powdery mildew diseases; thus, they can be used for combating Podosphaera species, such as, for example, against the powdery mildew of apple causative organism (*Podosphaera leucotricha*), and Erysiphe species, such as, for example, against the powdery mildew of cucumber causative organism (*Erysiphe cichoriacearum*) or the powdery mildew of barley or powdery mildew of cereal causative organism (*Erysiphe graminis*); and for combating other cereal diseases, such as cereal rust. It should be particularly emphasised that the active compounds according to the invention not only develop a protective action, but in some cases also have a systemic action. Thus, it is possible to protect plants against fungal attack when the active compound is fed to the above-ground parts of the plant via the soil and the root or via the seed.

As plant protection agents, the active compounds according to the invention can be used for the treatment of seed or soil and for the treatment of above-ground parts of plants.

The active compounds can be converted into the customary formulations, such as solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention can be present in the formulations as a mixture with other active compounds, such as fungicides, insecticides, acaricides, nematicides, herbicides, bird repellents, growth factors, plant nutrients and agents for improving soil structure.

The active compounds can be used as such, as their formulations or as the use forms prepared therefrom by further dilution, such as ready-to-use solutions, emulsions, suspensions, powders, pastes and granules. They may be used in the customary manner, for example by watering, spraying, atomizing, dusting, scattering, dry dressing, moist dressing, wet dressing, slurry dressing or encrusting.

Especially when used as leaf fungicides, the active compound concentrations in the use forms can be varied within a fairly wide range. They are, in general, from 1 to 0.0001 percent by weight, preferably from 0.5 to 0.001%.

In the treatment of seed, amounts of active compound of 0.001 to 50 g, preferably 0.01 to 10 g, are generally employed per kilogram of seed.

For the treatment of soil, amounts of active compound of 0.00001 to 0.1 percent by weight, preferably 0.0001 to 0.02%, are generally employed at the place of action.

The present invention also provides a fungicidal composition containing as active ingredient a compound of the present invention in admixture with a solid or liquefied gaseous diluent or carrier or in admixture with a liquid diluent or carrier containing a surface-active agent.

The present invention also provides a method of combating fungi which comprises applying to the fungi, or to a habitat thereof, a compound of the present invention alone or in the form of a composition containing as active ingredient a compound of the present invention in admixture with a diluent or carrier.

The present invention further provides crops protected from damage by fungi by being grown in areas in which immediately prior to and/or during the time of the growing a compound of the present invention was applied alone or in admixture with a diluent or carrier.

It will be seen that the usual methods of providing a harvested crop may be improved by the present invention.

PREPARATIVE EXAMPLES

EXAMPLE 1

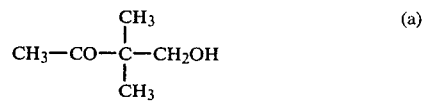

(a)

66 g (2.2 mol) of para-formaldehyde and 1 g of potassium hydroxide in 10 ml of methanol were added dropwise to 172 g (2 mol) of methyl isopropyl ketone in 1,000 ml of methanol. The mixture was heated under reflux for 15 hours and the methanol was then distilled off over a column at an internal temperature of 82° C. The residue was distilled under a waterpump vacuum. 152.7 g (68% of theory) of 2,2-dimethyl-1-hydroxy-butan-3-one of boiling point 80°–82° C./12 mm Hg were obtained.

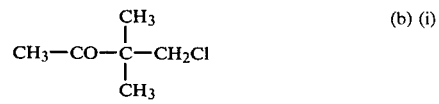

(b) (i)

11.6 g (0.1 mol) of 2,2-dimethyl-1-hydroxy-butan-3-one were added dropwise to 20.5 g (0.1 mol) of N,N-diethyl-1,2,2-trichlorovinylamine at 50° to 60° C. (cooling with ice). After stirring the mixture at 60° C. for two hours, it was distilled under a waterpump vacuum. 8.1 g (60% of theory) of 1-chloro-2,2-dimethyl-butan-3-one of melting point 60°–62° C./12 mm Hg were obtained.

(ii) 1-Chloro-2,2-dimethyl-butan-3-one was obtained in a yield of 90% when equimolar amounts of 2,2-dimethyl-1-hydroxy-butan-3-one and triphenylphosphine in ten times the amount of carbon tetrachloride were heated under reflux for 12 hours, the solvent was distilled off, the residue was taken up in ether and the ether mixture was filtered and distilled.

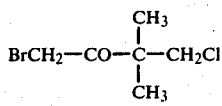
(c)

134.5 g (1 mol) of 1-chloro-2,2-dimethyl-butan-3-one were dissolved in 500 ml of ether. 51 ml (1 mol) of bromine were added dropwise at room temperature, while cooling slightly, at a rate such that it was continuously consumed. Thereafter, the solution was stirred into 1,000 ml of ice-water and the organic phase was separated off, rinsed with 250 ml of water, dried over sodium sulphate and distilled. 169 g (80% of theory) of 1-bromo-4-chloro-3,3-dimethyl-butan-2-one of boiling point 95°-106° C./13 mm Hg were obtained.

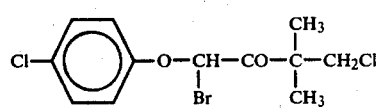
(d)

213.5 g (1 mol) of 1-bromo-4-chloro-3,3-dimethyl-butan-2-one were added dropwise to a boiling suspension of 128.5 g (1 mol) of 4-chlorophenol and 140 g (1 mol) of potassium carbonate in 1,000 ml of absolute acetone. The mixture was stirred under reflux for 15 hours and then allowed to cool and the inorganic residue was filtered off and rinsed with acetone. The filtrate was concentrated by distilling off the solvent in vacuo, the residue was taken up in 1,000 ml of methylene chloride and the methylene chloride mixture was washed three times with 250 ml of water each time, dried over sodium sulphate and distilled. 210 g (80.7% of theory) of 4-chloro-1-(4-chlorophenoxy)-3,3-dimethyl-butan-2-one of boiling point 125°-127° C./0.1 mm were obtained.

210 g (0.81 mol) of 4-chloro-1-(4-chlorophenoxy)-3,3-dimethyl-butan-2-one were dissolved in 1,000 ml of carbon tetrachloride. 41 ml (0.01 mol) of bromine were added dropwise at room temperature at a rate such that it was continuously consumed. The mixture was then stirred at room temperature for 30 minutes. After distilling off the solvent in vacuo, 268.3 g (98% of theory) of crude 1-bromo-4-chloro-1-(4-chlorophenoxy)-3,3-dimethyl-butan-2-one were obtained and were further reacted directly.

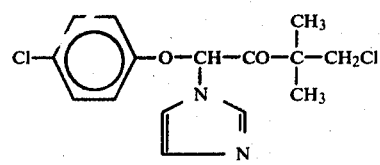
(e)

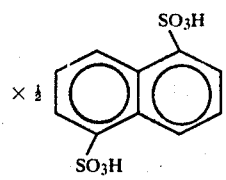

17 g (0.05 mol) of crude 1-bromo-1-(4-chlorophenoxy)-3,3-dimethyl-4-chloro-butan-2-one were dissolved in 100 ml of absolute acetonitrile. 12 g (0.175 mol) of imidazole were added to this solution and the mixture was heated under reflux for 40 hours. Thereafter, it was concentrated by distilling off the solvent in vacuo and the residue was taken up in 300 ml of methylene chloride. The methylene chloride mixture was washed three times with 100 ml of water each time, dried over sodium sulphate and concentrated again in vacuo. The residue was taken up in 100 ml of acetone, and a solution of 9 g (0.038 mol) of 1,5-naphthalenedisulphonic acid in 50 ml of acetone was added. After 2 hours, the precipitate which had formed was filtered off and dried. 19.8 g (80.7% of theory) of 1-(4-chlorophenoxy)-1-(imidazol-1-yl)-3,3-dimethyl-4-chloro-butan-2-one naphthalene-1,5-disulphonate of melting point 266°-267° C. were obtained.

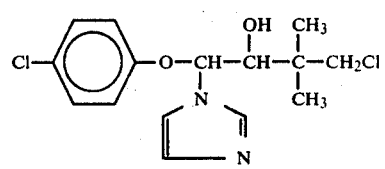
(f)

18.8 g (0.04 mol) of 1-(4-chlorophenoxy)-1-(imidazol-1-yl)-3,3-dimethyl-4-chloro-butan-2-one naphthalene-1,5-disulphonate were suspended in 100 ml of methylene chloride, and 100 ml of sodium bicarbonate solution were added. The organic phase was separated off, dried over sodium sulphate and concentrated by distilling off the solvent in vacuo. The base thus obtained was taken up in 100 ml of isopropanol, and 2 g (0.05 mol) of sodium borohydride were added in portions at 5° to 10° C. The mixture was stirred at room temperature for 15 hours and the isopropanol was then distilled off. The residue was taken up in 100 ml of methylene chloride and, after adding 100 ml of water, the mixture was stirred at room temperature for a further 15 hours. The organic phase was then separated off, washed twice with 50 ml of water each time, dried over sodium sulphate and concentrated. The oil which remained was boiled up in 100 ml of petroleum ether, whereupon crystallization occurred. 9.8 g (75% of theory) of 1-(4-chlorophenoxy)-1-(imidazol-1-yl)-3,3-dimethyl-4-chloro-butan-2-ol of melting point 120°-125° C. were obtained.

Process variant (a)

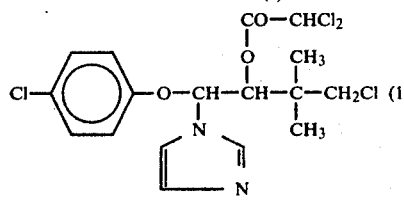
(g)

19.8 g (0.06 mol) of 1-(4-chlorophenoxy)-1-(imidazol-1-yl)-3,3-dimethyl-4-chlorobutan-2-ol were added to 200 ml of dichloroacetyl chloride at 0° C. The mixture was stirred at room temperature for 24 hours and excess dichloroacetyl chloride was distilled off in vacuo. The oil which remained was taken up in 400 ml of methylene chloride, the methylene chloride mixture was neutralized with 500 ml of aqueous sodium bicarbonate solution, the organic phase was separated off, washed with 200 ml of water and dried over sodium sulphate. The solvent was distilled off and the residue was taken up in 200 ml of diisopropyl ether. After leaving the mixture to stand for several hours, colorless crystals precipitated. 7.5 g (29% of theory) of 1-(4-chlorophenoxy)-1-(imidazol-1-yl)-2-dichloroacetoxy-3,3-dimethyl-4-chloro-butane of melting point 108°–110° C. were obtained.

EXAMPLE 2

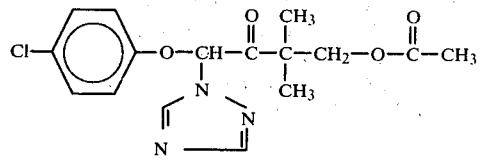
(a)

The compound 1-(4-chlorophenoxy)-1-(1,2,4-triazol-1-yl)-3,3-dimethyl-4-acetoxy-butan-2-one was obtained, starting from methyl isopropyl ketone, by formulation, esterification with acetic anhydride, bromination, nucleophilic substitution with p-chlorophenol, bromination and nucleophilic substitution with 1,2,4-triazole (see also DE-OS (German Published Specification) No. 2,635,666).

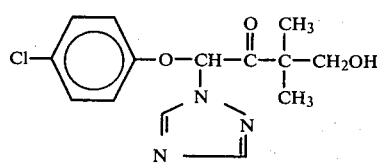
(b)

77.7 g (0.225 mol) of 1-(4-chlorophenoxy)-1-(1,2,4-triazol-1-yl)-3,3-dimethyl-4-acetoxy-butan-2-one were dissolved in 500 ml of methanol, 27 ml of concentrated hydrochloric acid were added and the mixture was heated under reflux for 8 hours. The solvent was distilled off under a waterpump vacuum, the residue was taken up in 500 ml of methylene chloride, the methylene chloride was stirred with 500 ml of aqueous saturated sodium bicarbonate solution, the organic phase was separated off and washed three times with 100 ml of water each time and the solvent was distilled off in vacuo. 200 ml of petroleum ether were added to the residue and the crystals which had precipitated were filtered off and dried at 40° C. in a circulating air drying cabinet.

60.8 g (87.5% of theory) of 1-(4-chlorophenoxy)-1-(1,2,4-triazol-1-yl)-3,3-dimethyl-4-hydroxy-butan-2-one of melting point 110°–111° C. were obtained.

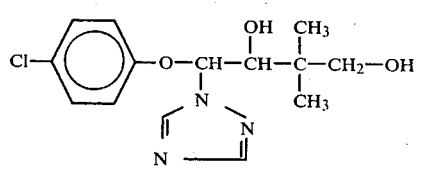
(c)

25 g (0.08 mol) of 1-(4-chlorophenoxy)-1-(1,2,4-triazol-1-yl)-3,3-dimethyl-4-hydroxy-butan-2-one were dissolved in 350 ml of isopropanol, and 3.5 g of sodium borohydride were added in portions at room temperature. The mixture was stirred at room temperature for 15 hours, 500 ml of water were added, the mixture was stirred at room temperature for a further 15 hours, 300 ml of methylene chloride were added and the organic phase was washed three times with 100 ml of water each time. The organic phase was dried over sodium sulphate, the solvent was distilled off under a waterpump vacuum and 100 ml of ether were added to the residue. 17 g (67.6% of theory) of 1-(4-chlorophenoxy)-1-(1,2,4-triazol-1-yl)-3,3-dimethyl-butane-2,4-diol were obtained as colorless crystals of melting point 110°–112° C.

Process variant (a)

(d)

46 g (0.123 mol) of 1-(4-chlorophenoxy)-1-(1,2,4-triazol-1-yl)-3,3-dimethyl-butane-2,4-diol were warmed to 50° C. with 16 g (0.205 mol) of acetyl chloride for about 16 hours. Therefore, 500 ml of methylene chloride and then 1,000 ml of saturated sodium bicarbonate solution were added. The mixture was stirred at room temperature for 1 hour and the organic phase was separated off, washed twice with 500 ml of water each time, dried over sodium sulphate and concentrated by distilling off the solvent in vacuo. The oil which remained was taken up in 300 ml of acetone, and 23 g of naphthalene-1,5-disulphonic acid were added. The precipitate which formed was filtered off and taken up in 600 ml of methylene chloride and the methylene chloride mixture was neutralized with 1,000 ml of saturated sodium bicarbonate solution. The organic phase was separated off, washed twice with 500 ml of water each time and dried over sodium sulphate. Thereafter, it was concentrated by distilling off the solvent in vacuo. The oil which remained crystallized after adding 100 ml of diisopropyl ether. 14 g (29% of theory) of 1-(4-chlorophenoxy)-1-(1,2,4-triazol-1-yl)-3,3-dimethyl-2,4-diacetoxy-butane of melting point 84°–87° C. were obtained.

EXAMPLE 3

Process variant (b)

23.1 g (0.07 mol) of 1-(4-chlorophenoxy)-1-(1,2,4-triazol-1-yl)-3,3-dimethyl-4-chloro-butan-2-ol were dissolved in 100 ml of acetic anhydride and the solution was heated to 100° C. for 12 hours. Thereafter, it was concentrated by distilling off excess acetic anhydride in vacuo. The oil which remained was taken up in 150 ml of diisopropyl ether and the product was allowed to crystallize out at 0° C. 17 g (65% of theory) of 1-(4-chlorophenoxy)-1-(1,2,4-triazol-1-yl)-2-acetoxy-3,3-dimethyl-4-chloro-butane of melting point 111°–117° were obtained.

The compounds in Table 1 which follows were obtained in a corresponding manner.

TABLE 1

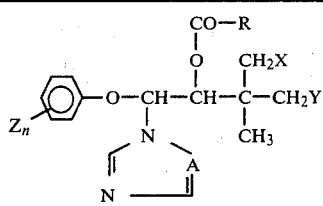

$$\text{Z}_n\text{—}\underset{\underset{N\diagdown\diagup A}{|}}{\bigcirc}\text{—O—CH—CH—}\underset{\underset{CH_3}{|}}{\overset{\overset{CO-R}{|}}{\underset{|}{C}}}\text{—CH}_2Y \quad (I)$$

with $CH_2X$ on the middle carbon.

| Compound No. | A | R | X | Y | $Z_n$ | Melting point (°C.) |
|---|---|---|---|---|---|---|
| 4 | N | —CHCl₂ | H | Br | 4-Cl | 97–100 |
| 5 | N | —CH₂Cl | H | Cl | 4-Cl | 123–125 |
| 6 | N | —CHCl₂ | H | Cl | 4-Cl | 74–80 |
| 7 | N | CH₃ | H | Br | 4-Cl | 101–106 |
| 8 | N | —CH₂Cl | H | Br | 4-Cl | 120–122 |
| 9 | CH | CH₃ | H | Cl | 4-Cl | 121–123 |
| 10 | CH | CH₃ | H | Br | 4-Cl | 188–191 (. ½ NDS) |
| 11 | N | CH₃ | H | Cl | 4-⬡ | 84–97 (B-form) |
| 12 | N | —NH—⬡ | H | Cl | 4-⬡ | 106–10 (decomp.) |
| 13 | N | —NH—⬡—Cl | H | Cl | 4-⬡ | 165–67 (A-form) |
| 14 | N | —NHCH₃ | H | Cl | 4-⬡ | 120–24 |
| 15 | N | —NHCH₃ | H | Br | 4-⬡ | 125–30 |
| 16 | N | —NHCH₃ | H | Cl | 4-Cl;2-CH₃ | 135–37 |
| 17 | N | —NHCH₃ | H | Br | 2-Cl | 120–23 |
| 18 | N | —NHCH₃ | H | Br | 4-Cl,2-CH₃ | 131–32 |
| 19 | N | —NHC₂H₅ | H | Cl | 4-⬡ | 106–09 |

NDS = naphthalene-1,5-disulphonic acid
A- and B-form: one of the two possible geometric isomeres.

The fungicidal activity of the compounds of this invention is illustrated by the following example wherein the compounds according to the present invention are each identified by the number (given in brackets) from the preparative examples hereinabove:

EXAMPLE 4

Shoot treatment test/powdery mildew of cereals (leaf-destructive mycosis)/protective To produce a suitable preparation of active compound, 0.25 part by weight of active compound was taken up in 25 parts by weight of dimethylformamide and 0.06 part by weight of alkylaryl polyglycol ether; 975 parts by weight of water were then added. The concentrate was diluted with water to the desired final concentration of the spray liquor.

To test for protective activity, single-leaved yound barley plants of the Amsel variety were sprayed with the preparation of active compound until dewmoist. After drying, the barley plants were dusted with spores of *Erysiphe graminis* var. *hordei*.

After 6 days' dwell time of the plants at a temperature of 21–22 deg.C and 80–90% atmospheric humidity the occurrence of mildew pustules on the plants was evaluated. The more active the compound, the lower was the degree of mildew infection.

In this test, for example, the following compounds exhibited a very good action which was superior to that of the compounds known from the prior art: (4), (3), (5) and (6).

EXAMPLE 5

Powdery mildew of barley (*Erysiphe graminis* var. *hordei*) (fungal disease of cereal shoots)/systemic The active compound was used as a pulverulent seed treatment agent. This was prepared by extending the particular active compound with a mixture of equal parts by weight of talc and kieselguhr to give a finely pulverulent mixture of the desired concentration of active compound.

For the treatment of seed, barley seed was shaken with the extended active compound in a closed glass bottle. The seed was sown at the rate of 3×12 grains in flowerpots, 2 cm deep in a mixture of one part by volume of Fruhstorfer standard soil and one part by volume of quartz sand. The germination and emergence took place under favourable conditions in a greenhouse. 7 days after sowing, when the barley plants had developed their first leaf, they were dusted with fresh spores of *Erysiphe graminis* var. *hordei* and grown on at 21–22 deg.C and 80–90% relative atmospheric humidity and 16 hours' exposure to light. The typical mildew pustules formed on the leaves over the course of 6 days. The more active the compound, the lower was the degree of mildew infection.

In this test, for example, the following compounds exhibited a very good action which is superior to that of the compounds known from the prior art: (4), (3), (5), (6), (7), (8), (9) and (10).

EXAMPLE 6

Shoot treatment test/cereal must (leaf-destructive mycosis)/protective

To produce a suitable preparation of active compound, 0.25 part by weight of active compound was taken up in 25 parts by weight of dimethylformamide and 0.06 part by weight of alkylaryl polyglycol ether and then 975 parts by weight of water were added. The concentrate was diluted with water to the desired final concentration of the spray liquor.

To test the protective activity, one-leaved young wheat plants of the Michigan Amber variety were inoculated with a uredosore suspension of *Puccinia recondita* in 0.1% strength aqueous agar. After the spore suspension had dried on, the wheat plants were sprayed with the preparation of active compound until dew-moist and were placed, for incubation, in a greenhouse for 24 hours at about 20 deg.C and 100% relative atmospheric humidity.

After 10 days' dwell time of the plants at a temperature of 20 deg.C and 80–90% atmospheric humidity, the occurrence of rust pustules on the plant was evaluated. The more active the compound, the lower was the degree of rust infection.

In this test, for example, the following compounds exhibited a very good action, which was significantly superior to that of the compounds known from the prior art: (4), (3), (6), (7), (9), (1) and (10).

EXAMPLE 7

Erysiphe test (cucumber)/protective
Solvent: 4.7 parts by weight of acetone
Emulsifier: 0.3 part by weight of alkylaryl polyglycol ether
Water: 95 parts by weight The amount of the active compound required for the desired concentration of active compound in the spray liquid was mixed with the stated amount of solvent and the concentrate was diluted with the stated amount of water containing the stated amount of emulsifier.

Young cucumber plants with about three foliage leaves were sprayed with the spray liquid until dripping wet. The cucumber plants remained in a greenhouse for 24 hours to dry. They were then, for the purpose of inoculation, dusted with conidida of the fungus *Erysiphe cichoriacearum*. The plants were subsequently placed in a greenhouse at 23–24 degrees C and at a relative atmospheric humidity of about 75%.

After 12 days, the infection of the cucumber plants was determined.

In this test, for example, the following compounds exhibited a very good action, which was superior to that of the compounds known from the prior art: (4), (3), (2), (5), (6), (7), (8), (9), (1) and (10).

EXAMPLE 8

Podosphaera test (apple)/protective
Solvent: 4.7 parts by weight of acetone
Emulsifier: 0.3 part by weight of alkylaryl polyglycol ether
Water: 95 parts by weight The amount of active compound required for the desired concentration of the active compound in the spray liquid was mixed with the stated amount of solvent, and the concentrate was diluted with the stated amount of water which contained the stated amount of emulsifier.

Young apple seedlings in the 4–6 leaf stage were sprayed with the spray liquid until dripping wet. The plants remained in a greenhouse for 24 hours at 20 deg.C and at a relative atmospheric humidity of 70%. They were then inoculated by dusting the conidia of the apple powdery mildew causative organism (*Podosphaera leucotricha*) and placed in a greenhouse at a temperature of 21–23 deg. C and at a relative atmospheric humidity of about 70%.

10 days after the inoculation, the infection of the seedlings was determined.

In this test, for example, the following compounds exhibited a very good action, which was superior to that of the compounds known from the prior art: (4), (3), (5), (6), (7) and (8).

It will be appreciated that the instant specification and examples are set forth by way of illustration and not limitation, and that various modifications and changes may be made without departing from the spirit and scope of the present invention.

What is claimed is:

1. A 2-acyloxy-1-azolyl-3,3-dimethyl-2-phenoxybutane of the formula

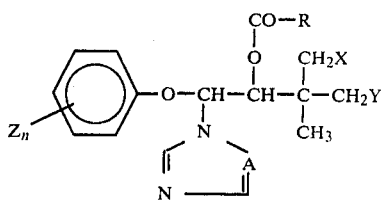

in which
A represents a nitrogen atom or the CH group,
R represents alkyl with 1 to 8 carbon atoms; alkenyl or alkynyl with 2 to 4 carbon atoms; halogenomethyl or halogenoethyl with 1 to 5 halogen atoms; alkoxyalkyl with 1 to 4 carbon atoms in each alkyl moiety; cycloalkyl with 5 to 7 carbon atoms; phenyl, benzyl, phenethyl, phenoxymethyl or phenoxyethyl optionally carrying at least one substituent on the phenyl nucleus selected from halogen, cyano, nitro, methyl and ethyl; alkylamino with 1 to 12 carbon atoms; dialkylamino with 1 to 4 carbon atoms in each alkyl moiety; halogenoalkylamino with up to 4 carbon atoms and up to 5 halogen atoms; alkoxycarbonylamino with 1 to 4 carbon atoms in the alkyl moiety, alkoxyalkylamino with 1 to 4 carbon atoms in each alkyl moiety; or phenylamino which optionally carries at least one substituent selected from halogen, nitro, cyano, alkyl with 1 to 4 carbon atoms, alkoxy and alkylthio with in either case 1 or 2 carbon atoms, halogenomethyl or halogenoethyl with up to 5 halogen atoms, and alkoxycarbonylalkenyl with 1 to 4 carbon atoms in the alkyl moiety and 2 to 4 carbon atoms in the alkenyl moiety;
X represents hydrogen, halogen or alkylcarbonyloxy with 1 to 4 carbon atoms in the alkyl moiety;
Y represents halogen;
Z represents halogen; cyano; nitro; alkyl with 1 to 4 carbon atoms; cycloalkyl with 5 to 7 carbon atoms; halogenomethyl or halogenoethyl with up to 5 halogen atoms; alkoxycarbonyl with a total of up to 5 carbon atoms; methoxy; ethoxy; methylthio; ethylthio; phenyl or phenoxy optionally carrying at least one substituent selected from halogen, amino, cyano, nitro, methyl and ethyl, or benzyl or phenethyl optionally substituted in the alkyl moiety by alkylcarbonyloxy with a total of up to 3 carbon atoms and in the phenyl ring by halogen, nitro or cyano; and
n represents 0, 1, 2, 3, 4 or 5, the substituents Z being selected independently of one another when n is 2 or more, or a physiologically acceptable acid addition salt or metal salt complex thereof.

2. A compound, salt or complex thereof according to claim 1, in which
A represents a nitrogen atom, and
R represents alkenyl or alkynyl with 2 to 4 carbon atoms; halogenomethyl or halogenoethyl with 1 to 5 halogen atoms; alkoxyalkyl with 1 to 4 carbon atoms in each alkyl moiety; cycloalkyl with 5 to 7 carbon atoms; phenyl, benzyl, phenethyl, phenoxymethyl or henoxyethyl optionally carrying at least one substituent on the phenyl nucleus selected from halogen, cyano, nitro, methyl and ethyl; alkylamino with 1 to 12 carbon atoms; dialkylamino with 1 to 4 carbon atoms in each alkyl moiety; halogenoalkylamino with up to 4 carbon atoms and up to 5 halogen atoms; alkoxycarbonylamino with 1 to 4 carbon atoms in the alkyl moiety, alkoxyalkylamino with 1 to 4 carbon atoms in each alkyl moiety; or phenylamino which optionally carries at least one substituent selected from halogen, nitro, cyano, alkyl with 1 to 4 carbon atoms, alkoxy and alkylthio with in either case 1 or 2 carbon atoms, halogenomethyl or halogenoethyl with up to 5 halogen atoms, and alkoxycarbonylalkenyl with 1 to 4 carbon atoms in the alkyl moiety and 2 to 4 carbon atoms in the alkenyl moiety.

3. A compound according to claim 2, in which R represents halogenomethyl or halogenoethyl with 1 to 5 halogen atoms.

4. A compound, or a salt or complex thereof, according to claim 1, wherein such compound is 1-(4-chlorophenoxy)-1-(1,2,4-triazol-1-yl)-2-acetoxy-3,3-dimethyl-4-chloro-butane of the formula

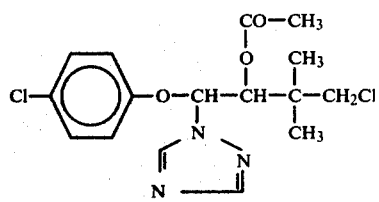

5. A compound, or a salt or complex thereof, according to claim 1, wherein such compound is 1-(4-chlorophenoxy)-1-(1,2,4-triazol-1-yl)-2-dichloroacetoxy-3,3-dimethyl-4-bromo-butane of the formula

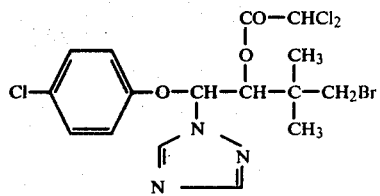

6. A compound, or a salt or complex thereof, according to claim 1, wherein such compound is 1-(4-chlorophenoxy)-1-(1,2,4-triazol-1-yl)-2-chloroacetoxy-3,3-dimethyl-4-chloro-butane of the formula

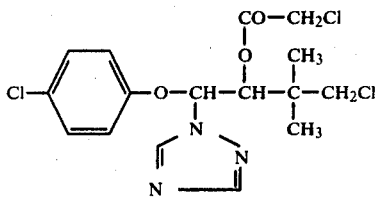

7. A comound, or a salt or complex thereof, according to claim 1, wherein such compound is 1-(4-chlorophenoxy)-1-(1,2,4-triazol-1-yl)-2-dichloroacetoxy-3,3-dimethyl-4-chloro-butane of the formula

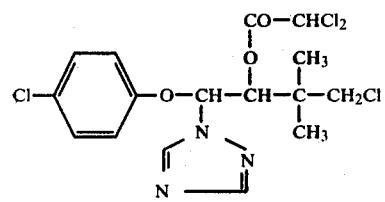

8. A compound, or a salt or complex thereof, according to claim 1, wherein such compound is 1-(4-chlorophenoxy)-1-(1,2,4-triazol-1-yl)-2-acetoxy-3,3-dimethyl-4-bromo-butane of the formula

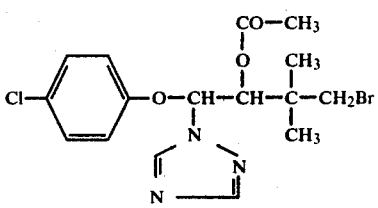

9. A fungicidal composition containing as active ingredient a fungicidally effective amount of a compound, salt or complex according to claim 1, in admixture with a diluent.

10. A method of combating fungi which comprises applying to the fungi, or to a habitat thereof, a fungicidally effective amount of a compound, salt or complex according to claim 1.

11. The method according to claim 10, in which said compound is
1-(4-chlorophenoxy)-1-(1,2,4-triazol-1-yl)-2-acetoxy-3,3-dimethyl-4-chloro-butane,
1-(4-chlorophenoxy)-1-(1,2,4-triazol-1-yl)-2-dichloroacetoxy-3,3-dimethyl-4-bromo-butane,
1-(4-chlorophenoxy)-1-(1,2,4-triazol-1-yl)-2-chloroacetoxy-3,3-dimethyl-4-chloro-butane,
1-(4-chlorophenoxy)-1-(1,2,4-triazol-1-yl)-2-dichloroacetoxy-3,3-dimethyl-4-chloro-butane, or
1-(4-chlorophenoxy)-1-(1,2,4-triazol-1-yl)-2-acetoxy-3,3-dimethyl-4-bromo-butane.

* * * * *